US006976999B2

(12) United States Patent
Charlebois et al.

(10) Patent No.: US 6,976,999 B2
(45) Date of Patent: Dec. 20, 2005

(54) PROSTHETIC DEVICE AND METHOD OF MAKING THE SAME

(75) Inventors: Steven Charlebois, Goshen, IN (US); Cheryl Blanchard, Warsaw, IN (US); Michael Hawkins, Columbia City, IN (US); Dale Swarts, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 184 days.

(21) Appl. No.: 10/299,435

(22) Filed: Nov. 19, 2002

(65) Prior Publication Data

US 2004/0098127 A1 May 20, 2004

(51) Int. Cl.[7] .............................................. A61F 2/28
(52) U.S. Cl. ............................. 623/16.11; 623/22.11
(58) Field of Search ......................... 623/16.11, 18.11, 623/22.11, 22.17, 22.19, 22.23, 22.24, 22.28, 623/22.15, 22.21

(56) References Cited

U.S. PATENT DOCUMENTS

| | | | | |
|---|---|---|---|---|
| 3,894,297 A | * | 7/1975 | Mittelmeier et al. ...... | 623/22.14 |
| 4,778,474 A | * | 10/1988 | Homsy .................... | 623/22.14 |
| 5,326,354 A | * | 7/1994 | Kwarteng ................ | 427/2.24 |
| 5,645,594 A | * | 7/1997 | Devanathan et al. ...... | 623/11.11 |
| 6,087,553 A | * | 7/2000 | Cohen et al. ............ | 623/22.21 |
| 6,096,083 A | * | 8/2000 | Keller et al. ............ | 623/22.11 |
| 6,368,354 B2 | * | 4/2002 | Burstein et al. ......... | 623/22.28 |
| 6,610,097 B2 | * | 8/2003 | Serbousek et al. ....... | 623/22.24 |

FOREIGN PATENT DOCUMENTS

| | | | | |
|---|---|---|---|---|
| DE | 297 04 605 U | | 5/1997 | |
| EP | 0 343 511 A | | 11/1989 | |
| EP | 0 554 214 A | | 8/1993 | |
| EP | 0 648 478 A | | 4/1995 | |
| EP | 648478 | * | 4/1995 | .............. 623/16.11 |
| EP | 0 681 845 A | | 11/1995 | |
| EP | 0 803 234 A | | 10/1997 | |
| EP | 803234 | * | 10/1997 | .............. 623/16.11 |
| GB | 2126096 | * | 3/1984 | ................ 623/16.1 |
| GB | 2126096 A | | 3/1984 | |
| WO | WO 01 24739 A | | 4/2001 | |

* cited by examiner

Primary Examiner—Pedro Philogene
(74) Attorney, Agent, or Firm—Jonathan D. Feuchtwang; Zimmer Technology, Inc.

(57) ABSTRACT

A method of making a non-modular prosthetic device for a joint arthroplasty. The method comprises molding a polymer interlayer between a porous metal structure and a polymer insert, wherein the insert generally comprises conventional or cross-linked ultra high molecular weight polyethylene ("UHMWPE").

10 Claims, 4 Drawing Sheets

PROSTHETIC DEVICE AND METHOD OF MAKING THE SAME

BACKGROUND

1. Field of the Invention

The present invention is related generally to prosthetic orthopedic implants, particularly to joint components such as for use with knees, hips, shoulders, elbows, toes, fingers, wrists, ankles, spinal discs and the like. More specifically, the present invention relates to a method of making a non-modular prosthetic joint component having a polymer, ceramic, or metal bearing component bonded to a polymer, ceramic, or metallic substrate having at least one porous surface.

2. Description of the Related Art

Orthopedic implant devices known to those of skill in the art often comprise a backing component and bearing component attached thereto. Furthermore, it is often desirable for the metal backing component to comprise a porous structure or surface suitable for bone ingrowth after the prosthetic devise is implanted. For example, a typical prosthetic acetabular cup comprises a hemispherical metal backing having a porous convex exterior and a solid concave interior. A similarly hemispherical, but smaller, polymer bearing surface is inserted into to the concave interior of the backing. In another example, a typical tibial component for use during a knee arthroplasty comprises metal tibial plateau having a porous bone contacting surface and a polymer bearing component attached to an opposing surface.

In many instances, prosthetic joint devices are modular. A modular device comprises a backing component, generally comprising a biocompatible metal having a porous structure or surface, and a separate bearing surface component, generally comprising a polymer. For example, a modular acetabular cup comprises a metal backing component and a polymer bearing surface fixedly inserted therein. Such fixation may be achieved via any of one or more of a variety of known mechanical means, such as snap fitting the components, press fitting the components, threadably connecting the components, using a locking ring, etc.

Those of skill in the art recognized that these additional mechanical retaining means could be avoided by using non-modular ("monoblock") joint components. Monoblock joint components comprise a metal backing such as a metal acetabular shell or a metal tibial plateau with the bearing surface integrally attached thereto. Unlike a modular component, the bearing surface of a monoblock is integral with the bearing component and need not be mechanically attached to the metal backing of an implant during an intraoperative step. There are several monoblock prosthetic devices presently available. These devices are generally produced by directly compression molding a thermoplastic polymer bearing component onto a backing component. However, this method of producing monoblock devices has disadvantages.

More recently, the bearing components of traditional monoblock prosthetic devices often comprise cross-linked ultra high molecular weight polyethylene ("UHMWPE"). Cross linking can be accomplished chemically, but it is usually accomplished via gamma or electron beam irradiation after the monoblock device is assembled. A problem with this process is that the metal component of the monoblock device can shield the bearing component from the electron beam radiation used to initiate cross linking, thereby making cross linking of the bearing component more difficult and time consuming or possibly having areas within the polymer remaining uncrosslinked.

Another problem with monoblock processes known in the art is that such processes do not accommodate using non moldable materials such as metals or ceramics for the bearing surface, as the same cannot be compression or injection molded onto a backing component.

Thus, a need exists for a method of making a monoblock orthopedic joint device, wherein the polymer component can be cross-linked separately from the backing component and subsequently connected to thereto to form a monoblock device.

A still further need exists for a method of making a monoblock orthopedic joint utilizing a metal, ceramic or other non-flowable material for the bearing surface.

SUMMARY

The present invention comprises a novel method of making a monoblock prosthetic joint device having a polymer, metal, or ceramic bearing component fixedly attached to a porous metal component or a metal component. In such devices, the metal component is generally in communication or contact with an adjacent bone. The bearing surface (or articular surface) is generally in movable contact with another bone or an articular surface from an adjacent implant.

An advantage of the present invention is that a cross-linked polymer component may be attached to a metal component rather than attaching a non-cross-linked polymer and subsequently irradiating the same to create cross-links as the metal component may make such subsequent irradiation difficult.

Another advantage of the present invention is that the bearing surface may comprise a variety of materials, such as, thermoplastics, thermosets, metals, and ceramics, yet still be bonded the porous metal component.

These and other advantages and features of the present invention will be apparent to those skilled in the art upon review of the appended claims and drawings.

BRIEF DESCRIPTION OF THE DRAWINGS

The above-mentioned and other features and objects of this invention, and the manner of obtaining them, will become more apparent and the invention itself will be better understood by reference to the following description of an embodiment of the invention taken in conjunction with the accompanying drawings, wherein.

Figure 1:
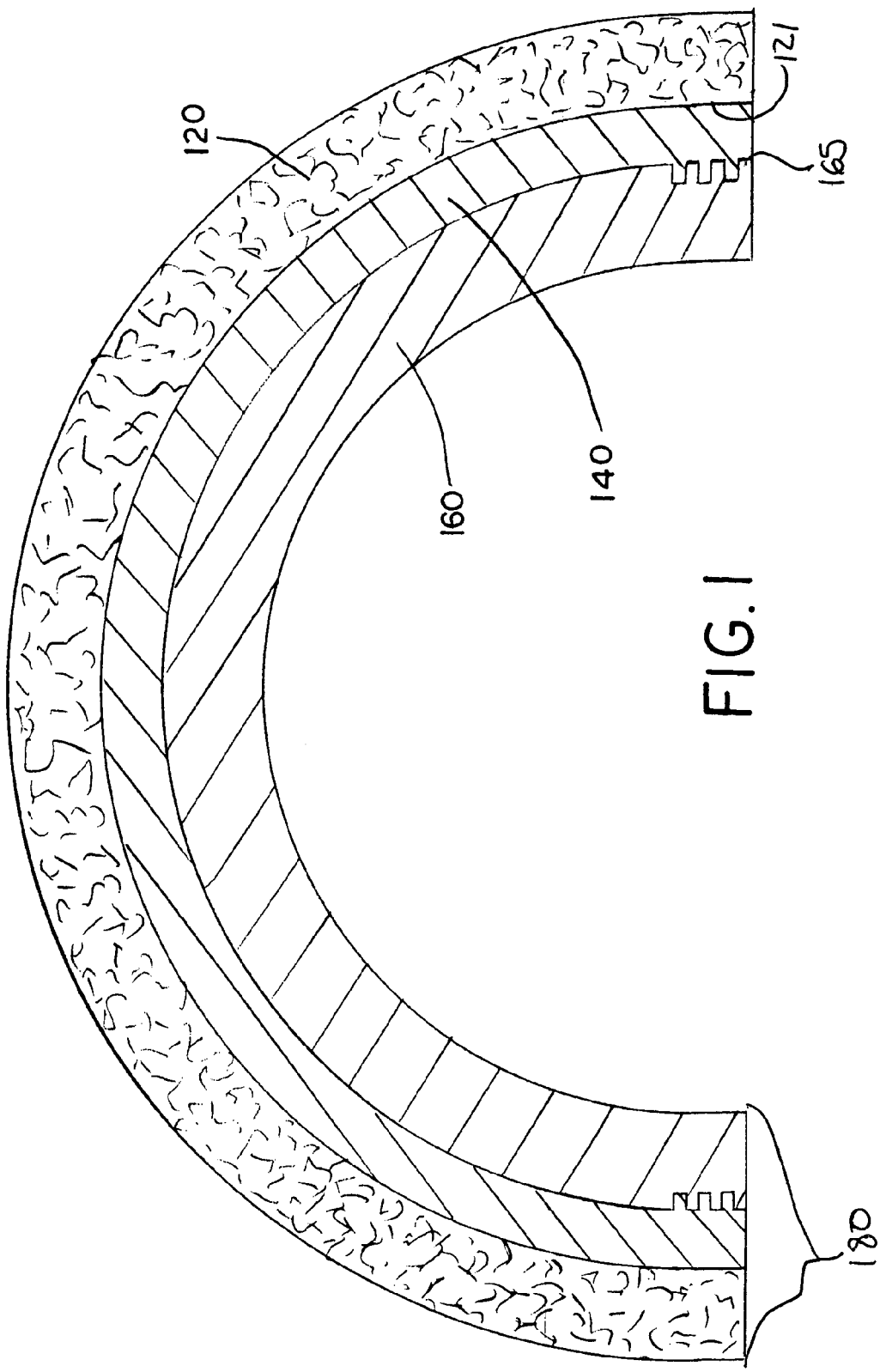
FIG. 1 is a side cross-sectional view of a prosthetic acetabular cup according to the present invention.

Corresponding reference characters indicate corresponding parts throughout the several views. Although the drawings represent an exemplary embodiment of the present invention, the drawings are not necessarily to scale and certain features may be exaggerated to better illustrate and explaining the invention. The exemplification set out herein illustrates an exemplary embodiment of the invention only.

DETAILED DESCRIPTION

Figure 2:
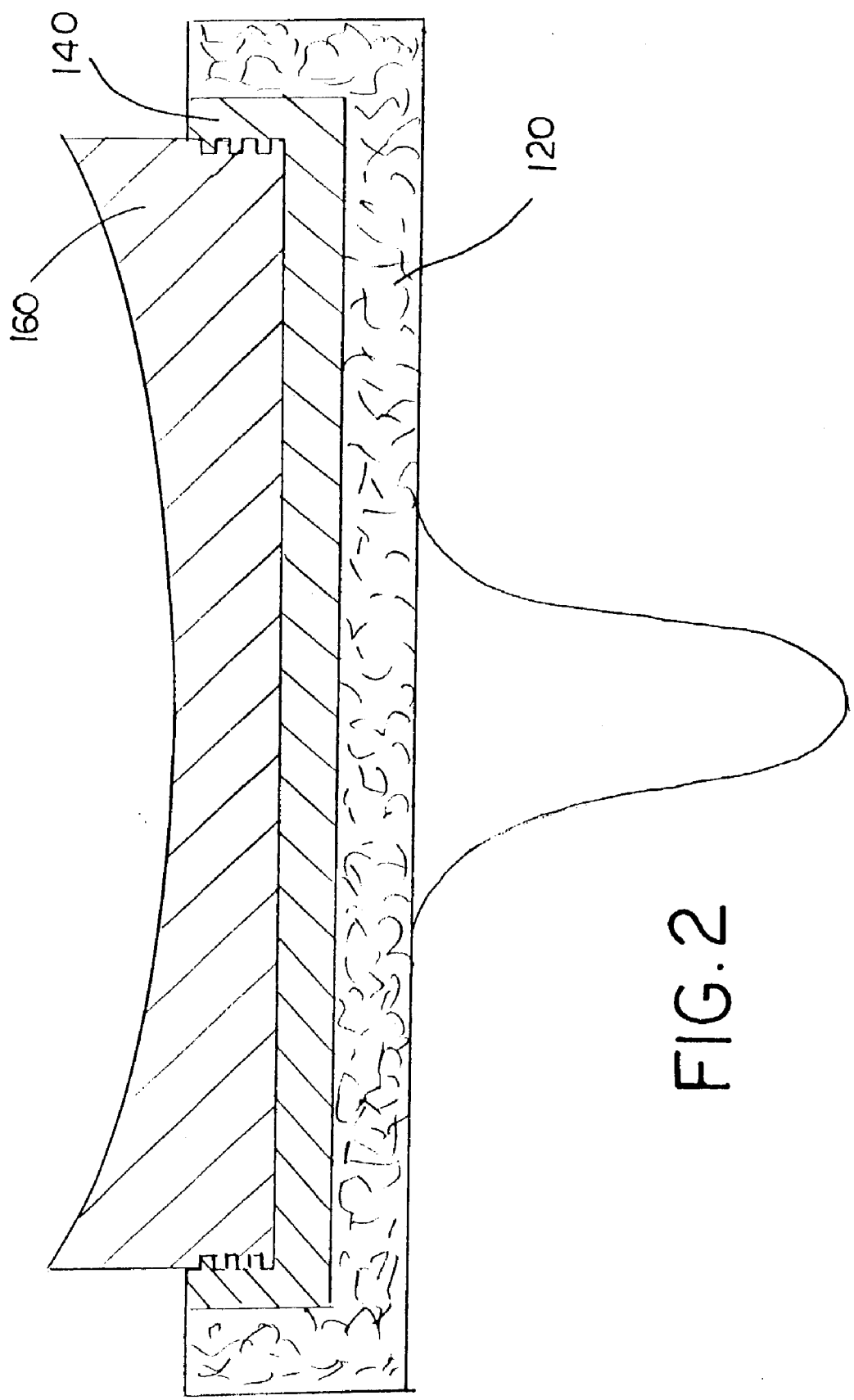
FIG. 2 is a side cross-sectional view of prosthetic knee tibial component according to the present invention.

The present invention comprises a method of making a monoblock prosthetic device, having a porous metal component. FIGS. 1 and 2 show exemplary devices that can be made using the present method, including an acetabular cup for a hip prosthesis and a tibial plateau for a knee prosthesis. It will be appreciated by those of skill in the art that other prosthetic devices comprising a metal component and bearing component, such as, glenoid components for shoulder prostheses and the like could also be made by the present method.

Figure 3:
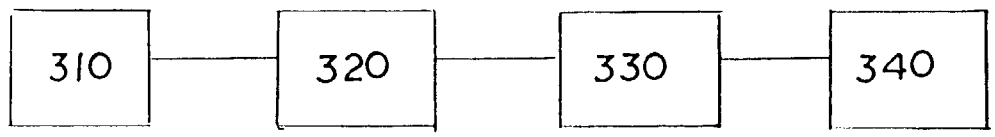
FIG. 3 is a diagrammatic view of a first embodiment of the present invention.

Referring now to FIG. 3, there is shown a diagrammatical view of a first embodiment 300 of the present method. The method comprises the steps of: providing metal backing component 120 of desired shape; providing a bearing component 160 of desired shape, said component having a plurality of grooves 165 disposed thereon; placing metal component 120 and bearing component 160 into an injection molding device, such that a desired gap exists between bearing component 160 and porous metal component 120; and injection molding a polymer interlayer 140 between porous metal component 120 and bearing component 160, such that polymer interlayer 140 is in communication with the porous structure of metal component 120 and grooves 165 of bearing component 160.

As used herein, the terms backing component 120, polymer interlayer 140, and bearing component 160, shall apply to such components generically without regard to a particular shape or prosthetic implant application. For example, the term bearing component 160 has equal application to the meniscus component of a knee prosthesis and to the articular surface of a prosthetic acetabular cup.

Figure 6:
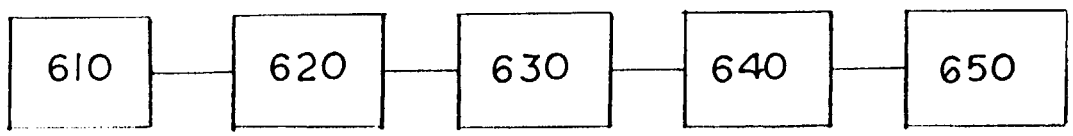
FIG. 6 is a diagrammatic view of a second embodiment of the present invention.

Referring again to FIG. 3, there is shown step 310 of method 300 comprising providing metal backing component 120. Metal backing component 120 comprises a textured surface 121 to which polymer interlayer 140 can attach. Preferably, metal backing 120 and surface 121 are entirely porous or surface 121 is porous and attached to metal backing 120 by means known commonly in the art. Alternatively, surface 121 of metal backing component 120 comprises a knurled surface, a roughened surface, or a grooved surface such that a mechanical bond can be created between interlayer 140 and surface 121. Metal component 120 comprises a biocompatible metal material selected from the group consisting of tantalum, titanium, cobalt chrome, and stainless steel. Metal backing component 120 is sufficiently porous to allow a polymer interlayer 140 to interdigitate therein (as shown in FIG. 6) during the molding process, described subsequently herein. Preferably, metal component 120 comprises a tantalum porous metal or a tantalum porous metal surface. An example of a suitable tantalum porous metal is disclosed in U.S. Pat. No. 5,282,861, entitled Open Cell Tantalum Structures for Cancellous Bone Implants and Cell and Tissue Receptors, issued on Feb. 1, 1994 to Richard B. Kaplan and assigned to Ultramet of Pomona, Calif., the disclosure of which is hereby incorporated by reference herein. Those of skill in the art will recognize that any biocompatible material having a surface of sufficient porosity and suitable mechanical properties to avoid being adversely affected by the present method can be used in the present invention. Some exemplary biocompatible materials include: stainless steel, cobalt chrome alloy, titanium, and titanium alloys.

Metal backing component 120 further comprises a shape appropriate for use in a particular orthopedic implant. For example, metal backing component 120 of step 310 could be shaped into a hemispherical shell for use in an acetabular cup implant as shown in FIG. 1. Alternatively, metal component 120 could be shaped into a plate for use as a tibial plateau, as shown in FIG. 2.

Referring still to FIG. 3, the method of the present invention further comprises step 320, wherein bearing component 160 of desired shape is provided. Bearing component 160 comprises a material selected from the group consisting of thermosets, thermoplastics, metals and ceramics, including, for example, polyurethane, polyethylene, and cross-linked polyethylene, titanium alloy, cobalt alloy, alumina, and zirconia. Bearing component 160 is shaped in a manner suitable for a particular orthopedic implant. For example, as shown in FIG. 1, bearing component 160 comprises a hemispherical shape that can be disposed within the concave interior of an acetabular cup shell. Alternatively, as shown in FIG. 2, bearing component 160 may, by way of example and not limitation, comprise a shape suitable for a prosthetic knee meniscus.

Figure 4:
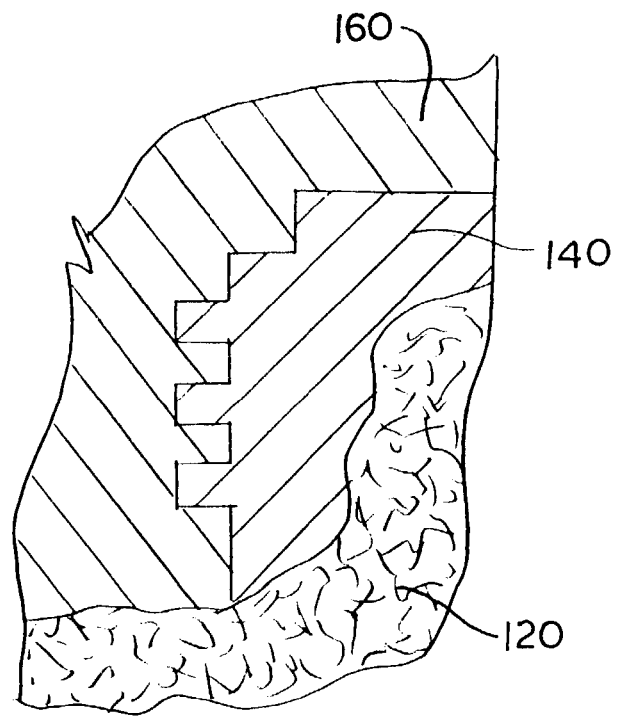
FIG. 4 is a front view of an interface according to the present invention.
Figure 5:
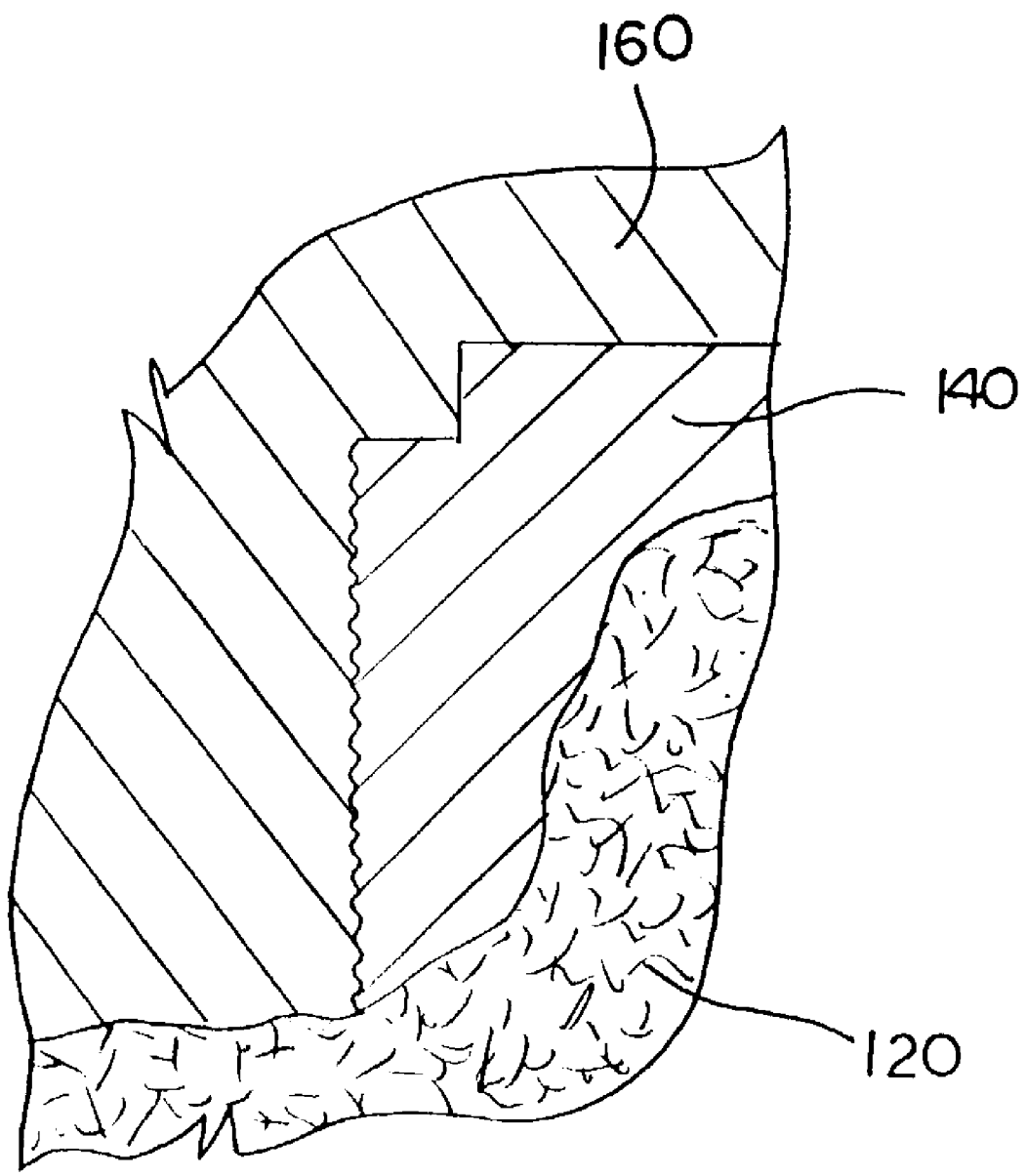
FIG. 5 is a front view of an interface according to an alternative embodiment of the present invention.

Referring now to FIG. 4, there is shown bearing surface 160. Bearing surface 160 comprises grooves 165 to which polymer interlayer 140 can attach or "interdigitate." In a first embodiment of the present invention, grooves 165 are disposed around a portion of the exterior of bearing component 160 such that metal component 120 may be at least partially disposed therearound as shown in FIG. 6, and described in more detail below. In other embodiments of the invention (FIG. 5) bearing component 160 may comprise in place of grooves, a textured surface, a knurled surface, or a surface having a plurality of machined or molded indentations, as shown in FIG. 5.

Referring again to FIG. 3, there is shown step 330 of method 300. Step 330 comprises placing porous backing component 120 and bearing component 160 into an injection molding device. Any injection molding device capable of transporting and curing a chosen polymer material is satisfactory. The molding device should also be capable of accommodating metal backing component 120 and bearing component 160 in its mold. Components 120 and 160 should be placed in the mold such that the at least one porous surface of metal component 120 faces a textured surface of bearing component 160. A gap of desired distance should exist within the mold between components 120 and 160.

Referring still to FIG. 3, there is shown step 340 of method 300, wherein a polymer interlayer 140 is thereafter injection molded into the gap. Interlayer 140 comprises any biocompatible thermoplastic polymer, including, for example, polyethylene, PEEK (a trademark polyketone of the Vitrex company); other polyketones; and polyurethane. During the injection molding process, interlayer 140 flows at least partially around the interlock means of bearing component 160 and at least partially into the porous surface of metal component 120. Upon curing, interlayer 140 mechanically locks itself to bearing component 160 and metal component 120, as illustrated in FIG. 6. Thus, a bond is created between components 120 and 160 via interlayer 140. Those of skill in the art will appreciate that it is preferable for interlayer 140 to comprise a polymer that is miscible with the material used for bearing component 160. For example, a polyethylene interlayer 140 should be used with cross-linked ultrahigh molecular weight polyethylene bearing components 160 because such interlayer 140 will provide an adhesive as well as a mechanical bond between interlayer 140 and bearing component 160.

Turning now to FIG. 6, there is shown another embodiment of the present invention, method 600. Method 600 comprises the steps of: providing a porous backing component 120 of desired shape; providing a bearing component 160 of desired shape, said component having polymer interlock means 165; placing the porous backing structure and the bearing component into a compression molding device, such that a desired gap exists between the bearing component and the porous structure; placing a layer of polymer resin in the gap between the porous surface of the backing component and the textured surface of the bearing component, such that the polymer layer is in communication with the porous structure and the textured surface of the bearing component, thereby forming an assembly; and subjecting the assembly to a compression molding cycle such that the polymer layer forms a solid interlayer, wherein the interlayer bonds the porous structure and the bearing component.

The steps of method 600 are as described above with regard to other embodiments of the present invention except for steps 640 and 650 described subsequently herein. Step 640 of method 500 comprises placing a polymer resin in a compression molding device adjacent to and in communication with a porous surface of backing component 120 and in communication with a textured surface of bearing component 160. This polymer resin will act as polymer interlayer 140. Those of skill in the art will appreciate that interlayer 140 may be provided in any usable form, including for example flakes or powder. Polymer interlayer 140 may, as disclosed previously herein, comprise any biocompatible thermoplastic polymer, including PEEK (a trademarked polyketone of the Vitrex company); poly ethylene, UHMWPE, polyurethane, and the like. The combination of interlayer 140 in communication with metal component 120 and bearing component 160 is referred to herein as assembly 180.

Referring still to FIG. 6, there is shown step 650 of method 600 in which assembly 180 is subjected to a compression molding cycle such that interlayer 140 flows into the porous surface of metal component 120 and around interlock means 165 of bearing component 160, respectively. The compression molding cycle generally comprises utilizing a pressure from about 100 psi to about 600 psi for a time of about 1 to about 6 hours; and a temperature from about 150° C. to about 200° C. Interlayer 140 mechanically secures itself into these surfaces as illustrated in FIGS. 4–5. After molding is complete, a near finished orthopedic implant has been produced.

In prior art methods of creating a monoblock prosthetic device, non-cross-linked material was molded directly to the porous surface of the metal component. In order to produce an implant having a cross-linked polymer bearing surface material the cross-linking is performed after the implant is assembled by irradiating the part. However, it is difficult to achieve uniform cross-link density using such practices because the metal component disrupts electron beam or gamma radiation that is generally used to initiate cross-linking in a polymer. An advantage, therefore, of the present method is that a bearing component comprising a cross-linked material may be bonded to a metal component without having to subsequently irradiate the part to cross-link the bearing component.

Another advantage of the present method is that it provides a means by which non-flowable materials may be used to form the bearing surface in that the bond between components 120 and 160 exists via interlayer 140. For example, the present method can bond a ceramic bearing component 160 having at least one textured or porous surface with a porous metal component 120.

It will be appreciated by those skilled in the art that the foregoing is a description of a preferred embodiment of the present invention and that variations in design and construction may be made to the preferred embodiment without departing from the scope of the invention as defined by the appended claims.

We claim:

1. A prosthetic implant comprising:
   a bearing component comprising a material selected from the group consisting of polymers, UHMWPE, polyethylene, polyurethane, and polyketone, the bearing component having an interlock means disposed on the exterior surface thereof;
   a backing component, the backing component having a textured surface; and
   a polymer interlayer disposed between the interlock means and the textured surface thereby connecting the bearing component to the backing component, wherein the bearing component and the interlayer are made of different materials.

2. The apparatus of claim 1, wherein the textured surface of the backing component is selected from the group consisting of a knurled surface, a roughened surface, a porous surface, and an adhesive surface.

3. The apparatus of claim 1, wherein the backing component comprises a material selected from the group consisting of tantalum, titanium, titanium alloy, stainless steel, cobalt chrome alloy, niobium, polymers, UHMWPE, polyethylene, polyurethane, polyketone, metals, cobalt chrome, titanium, tantalum, ceramics, alumina, and zirconia.

4. The apparatus of claim 1, wherein the polymer interlayer comprises a material selected from the group consisting of polyethylene, polyurethane, polyketone, and UHMWPE.

5. The apparatus of claim 1, wherein the interlock means is selected from the group consisting of a plurality of grooves disposed on the exterior of the bearing component, a knurled surface on the exterior of the bearing component, and an indented surface on the exterior of the bearing component.

6. A method of making a monoblock prosthetic device, the method comprising:
   providing a backing component of desired shape having at least one porous surface,
   providing a bearing component comprising a material selected from the group consisting of polymers, UHMWPE, polyethylene, polyurethane, and polyketone, said component having a polymer interlock means;
   molding a polymer interlayer between the at least one porous surface and the interlock means of the bearing component, such that the polymer layer is in communication with the at least one porous surface and the interlock means of the bearing component such that the interlayer affixes the backing component to the bearing component.

7. The method of claim 6, wherein the bearing component comprises a material selected from the group consisting of polymers, UHMWPE, polyethylene, polyurethane, polyketone, metals, cobalt chrome, titanium, tantalum, ceramics, alumina, and zirconia.

8. The method of claim 6, wherein the backing component comprises a material selected from the group consisting of tantalum, titanium, titanium alloy, stainless steel, cobalt chrome alloy, niobium, polymers, UHMWPE, polyethylene, polyurethane, polyketone, metals, cobalt chrome, titanium, tantalum, ceramics, alumina, and zirconia.

9. The method of claim 6, wherein the polymer interlayer comprises a material selected from the group consisting of polyethylene, polyurethane, polyketone, and UHMWPE.

10. The method of claim 6, wherein the interlock means is selected from the group consisting of a plurality of grooves disposed on the exterior of the bearing component, a knurled surface on the exterior of the bearing component, and an indented surface on the exterior of the bearing component.

* * * * *